United States Patent
Appling et al.

(10) Patent No.: US 7,826,904 B2
(45) Date of Patent: Nov. 2, 2010

(54) INTERSTITIAL MICROWAVE SYSTEM AND METHOD FOR THERMAL TREATMENT OF DISEASES

(75) Inventors: William M. Appling, Granville, NY (US); Giorgio di Palma, Queensbury, NY (US); Fred Sterzer, Princeton, NJ (US); Daniel D. Mawhinney, Livingston, NJ (US)

(73) Assignee: AngioDynamics, Inc., Latham, NY (US)

( * ) Notice: Subject to any disclaimer, the term of this patent is extended or adjusted under 35 U.S.C. 154(b) by 1213 days.

(21) Appl. No.: 11/348,980

(22) Filed: Feb. 7, 2006

(65) Prior Publication Data
US 2007/0185554 A1    Aug. 9, 2007

(51) Int. Cl.
*A61F 7/12*    (2006.01)
*A61N 5/02*    (2006.01)

(52) U.S. Cl. .................. 607/101; 607/116; 607/156; 606/33

(58) Field of Classification Search .......... 607/101, 607/116, 156; 606/33
See application file for complete search history.

(56) References Cited

U.S. PATENT DOCUMENTS

| | | | |
|---|---|---|---|
| 4,282,887 A | 8/1981 | Sterzer | |
| 4,557,272 A * | 12/1985 | Carr | 600/549 |
| 4,700,716 A * | 10/1987 | Kasevich et al. | 607/156 |
| 4,924,863 A | 5/1990 | Sterzer | |
| 4,967,765 A * | 11/1990 | Turner et al. | 607/154 |
| 5,007,437 A * | 4/1991 | Sterzer | 607/138 |
| 5,100,388 A * | 3/1992 | Behl et al. | 604/113 |
| 5,149,198 A | 9/1992 | Sterzer et al. | |
| 5,300,099 A | 4/1994 | Rudie | |
| 5,301,687 A * | 4/1994 | Wong et al. | 607/116 |
| 5,366,490 A | 11/1994 | Edwards et al. | |
| 5,405,346 A | 4/1995 | Grundy et al. | |
| 5,480,417 A | 1/1996 | Hascoet et al. | |
| 5,503,150 A | 4/1996 | Evans | |
| 5,507,743 A | 4/1996 | Edwards et al. | |
| 5,549,639 A | 8/1996 | Ross | |

(Continued)

FOREIGN PATENT DOCUMENTS

WO    WO 00/10472    3/2000

OTHER PUBLICATIONS

U.S. Appl. No. 10/337,159, filed Jan. 7, 2003, Sterzer et al.

(Continued)

*Primary Examiner*—Roy D Gibson
*Assistant Examiner*—Kaitlyn E Helling
(74) *Attorney, Agent, or Firm*—Tara L. Custer

(57) ABSTRACT

A minimally-invasive fluid-cooled insertion sleeve assembly, with an attached balloon and distally-located penetrating tip, into which sleeve any of a group comprising a rigid rod, a microwave-radiator assembly and an ultrasonic-imaging transducer assembly may be inserted, constitutes a probe of the system. The sleeve assembly comprises spaced inner and outer plastic tubes with two fluid channels situated within the coaxial lumen between the inner and outer tubes. The fluid coolant input flows through the fluid channels into the balloon, thereby inflating the balloon, and then exits through that coaxial lumen. An alternative embodiment has no balloon. The method employs the probe for piercing sub-cutaneous tissue and then ablating deep-seated tumor tissue with microwave-radiation generated heat.

26 Claims, 7 Drawing Sheets

U.S. PATENT DOCUMENTS

| | | | |
|---|---|---|---|
| 5,624,392 A * | 4/1997 | Saab | 604/43 |
| 5,688,050 A | 11/1997 | Sterzer et al. | |
| 5,737,384 A | 4/1998 | Fenn | |
| 5,776,176 A | 7/1998 | Rudie | |
| 5,800,486 A | 9/1998 | Thome et al. | |
| 5,843,144 A * | 12/1998 | Rudie et al. | 607/101 |
| 5,861,021 A | 1/1999 | Thome et al. | |
| 5,904,709 A * | 5/1999 | Arndt et al. | 607/101 |
| 5,949,845 A | 9/1999 | Sterzer et al. | |
| 5,992,419 A * | 11/1999 | Sterzer et al. | 128/898 |
| 6,097,985 A | 8/2000 | Kasevich et al. | |
| 6,181,970 B1 | 1/2001 | Kasevich | |
| 6,223,085 B1 | 4/2001 | Dann et al. | |
| 6,230,060 B1 | 5/2001 | Mawhinney | |
| 6,233,490 B1 | 5/2001 | Kasevich | |
| 6,312,428 B1 | 11/2001 | Eggers et al. | |
| 6,325,796 B1 | 12/2001 | Berube et al. | |
| 6,424,869 B1 | 7/2002 | Carr et al. | |
| 6,470,217 B1 | 10/2002 | Fenn et al. | |
| 6,640,139 B1 | 10/2003 | Ueberle | |
| RE38,299 E | 11/2003 | Bolmsjo | |
| 6,668,197 B1 | 12/2003 | Habib et al. | |
| 6,699,241 B2 | 3/2004 | Rappaport et al. | |
| 6,740,108 B1 | 5/2004 | Just et al. | |
| 6,847,848 B2 | 1/2005 | Sterzer et al. | |
| 6,866,624 B2 | 3/2005 | Chornenky et al. | |
| 6,878,147 B2 * | 4/2005 | Prakash et al. | 606/33 |
| 6,957,108 B2 | 10/2005 | Turner et al. | |
| 2001/0029368 A1 * | 10/2001 | Berube | 606/33 |
| 2002/0126568 A1 * | 9/2002 | Krumbock et al. | 366/91 |
| 2003/0065317 A1 * | 4/2003 | Rudie et al. | 606/33 |
| 2004/0133254 A1 * | 7/2004 | Sterzer et al. | 607/101 |
| 2004/0176826 A1 | 9/2004 | Martinelli | |
| 2005/0027335 A1 * | 2/2005 | Wakino et al. | 607/96 |
| 2005/0149010 A1 | 7/2005 | Turovskiy et al. | |
| 2005/0177209 A1 | 8/2005 | Leung et al. | |
| 2005/0228370 A1 | 10/2005 | Sterzer et al. | |
| 2007/0055224 A1 | 3/2007 | Lee, Jr. et al. | |
| 2007/0135877 A1 | 6/2007 | Pringle | |
| 2007/0203551 A1 | 8/2007 | Cronin et al. | |
| 2008/0033422 A1 * | 2/2008 | Turner et al. | 606/33 |
| 2009/0076497 A1 | 3/2009 | Morris et al. | |

OTHER PUBLICATIONS

Di Palma, et al.; "Treatment of Solid Malignant Tumors with Microwave Balloon Ablation Catheters and Localized Chemotherapy", Piers Online, vol. 3, No. 6, pp. 924-926, 2007, USA.

* cited by examiner

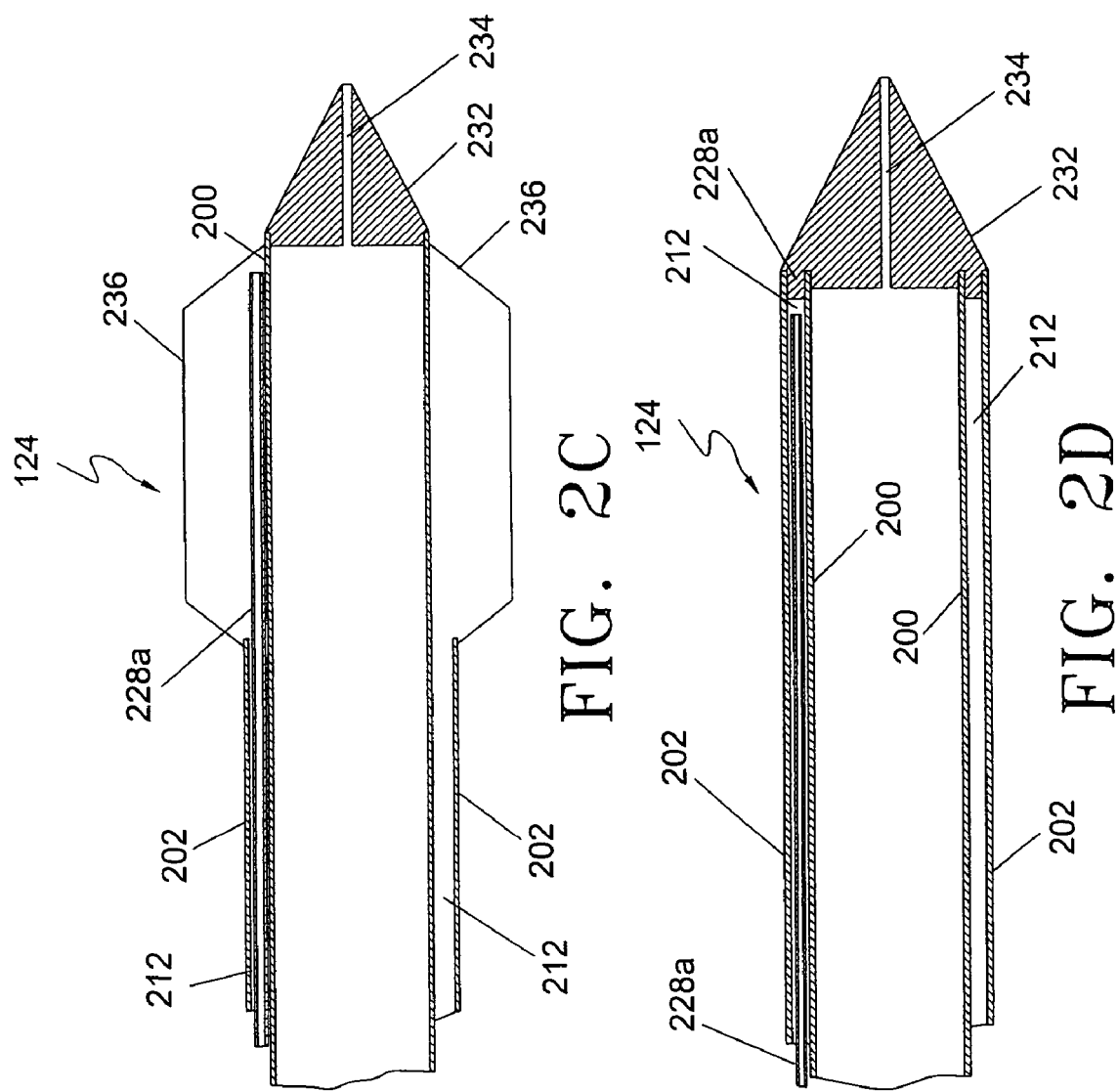

INTERSTITIAL MICROWAVE SYSTEM AND METHOD FOR THERMAL TREATMENT OF DISEASES

BACKGROUND

1. Field of the Invention

This invention relates to an interstitial microwave system and method of employing a minimally-invasive probe for thermally treating diseased tissue of a patient and, more particularly, to a probe comprising a fluid-coolable insertion-sleeve assembly into which any one of a plurality of separate functional structures may be inserted.

2. Description of the Prior Art

Incorporated by reference herein is U.S. Pat. No. 6,312,428 B1, issued Nov. 6, 2001, which discloses an interstitial system employing a minimally-invasive probe for thermally treating diseased tissue of a patient, but the system is not a microwave system and its probe comprises an integral structure that is not fluid cooled. Further, incorporated by reference herein is U.S. Pat. No. 6,847,848, issued Jan. 25, 2005 and assigned to MMTC, inc. one of the assignee in the present application, which discloses an interstitial microwave system employing a minimally-invasive catheter operating as a probe for thermally treating diseased tissue of a patient, but its probe comprises an integral structure that is fluid cooled, rather than comprising fluid-coolable insertion-sleeve assembly into which any one of a plurality of separate functional structures may be inserted. Further, this patent teaches the use of radiometer means for both monitoring the temperature of tissue being heated by microwave radiation and then using the monitored temperature to control such radiation to prevent overheating of this tissue.

SUMMARY OF THE INVENTION

The invention is directed to a minimally-invasive, fluid-coolable insertion-sleeve assembly into which any one of a group of separate individual insertable components, that includes an insertable microwave-radiator assembly component may be inserted, for use as a probe in an interstitial microwave system for thermally treating sub-cutaneous diseased tissue of a patient. Because the insertion-sleeve assembly may lack stiffness (if comprised of thin plastic tubing attached to a distally-located plastic penetrating point), the assembly may require that a rigid rod be inserted in the sleeve assembly to permit it to pierce the patient's skin and push through the underlying sub-cutaneous tissue to reach the diseased tissue. The rigid rod is then replaced by the microwave-radiator assembly, which is used to thermally treat the diseased tissue with microwave radiation. The microwave-radiator assembly may then be replaced by an inserted ultrasonic-imaging transducer assembly used to provide image display data of the treated tissue. The ultrasonic-imaging transducer assembly may also be used prior to treatment to provide a baseline display or during the treatment procedure.

BRIEF DESCRIPTION OF THE DRAWINGS

FIG. 2C shows the distal portion of the minimally-invasive, water-cooled insertion-sleeve assembly with an inflated balloon;

FIG. 2D shows an alternative embodiment of the distal portion of the minimally-invasive, water-cooled insertion-sleeve assembly without a balloon;

DETAILED DESCRIPTION

Figure 1:
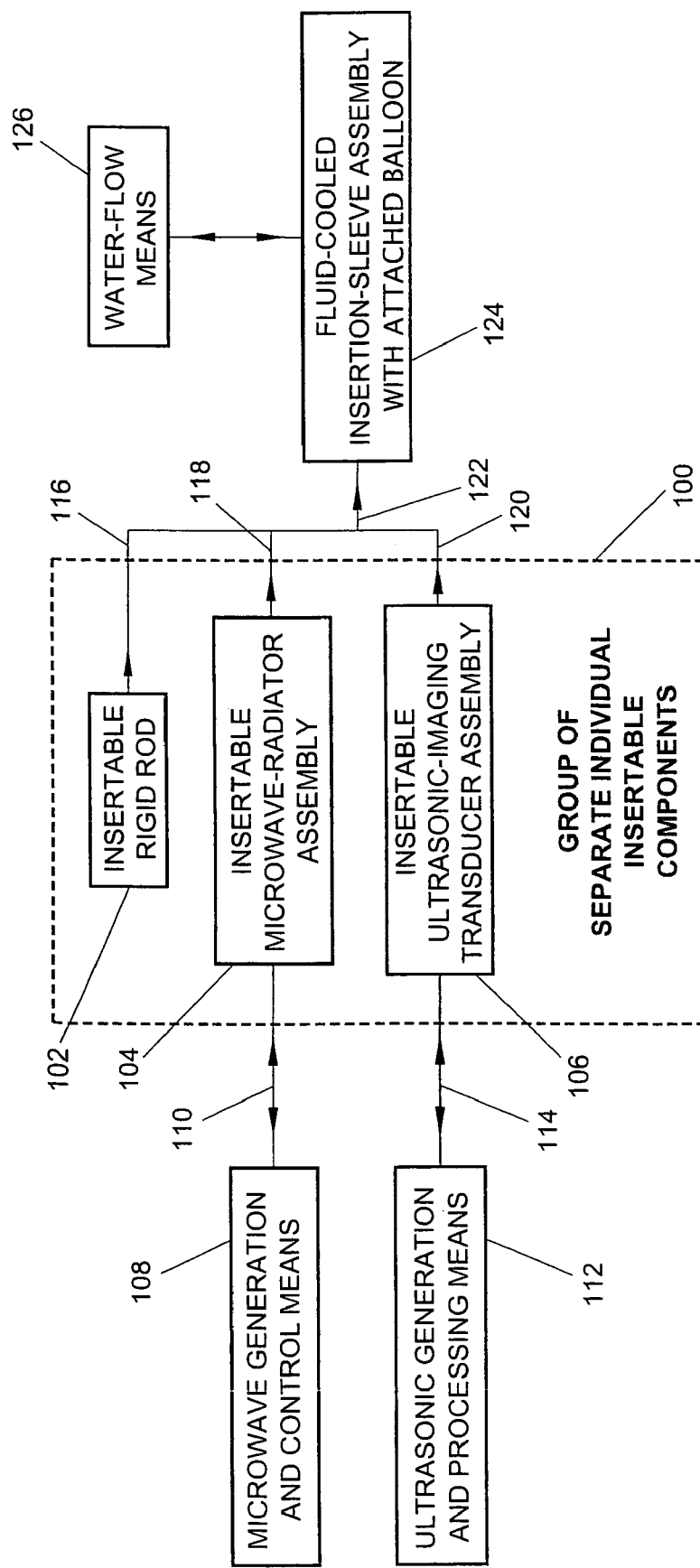
FIG. 1 is a functional block diagram of a microwave system that constitutes an illustrative embodiment of the present invention.

Referring to the FIG. 1 functional block diagram, there is shown a group of separate individual insertable components 100, which comprises insertable rigid rod 102, insertable microwave-radiator assembly 104 and insertable ultrasonic-imaging transducer assembly 106. Microwave energy from microwave generation and control means 108 is supplied to insertable microwave-radiator assembly 104 through connection 110. In practice, connection 110 normally comprises a standard 50 ohm impedance coaxial cable. Ultrasonic energy from ultrasonic generation and processing means 112 is supplied to insertable ultrasonic-imaging transducer assembly 106 through connection 114.

As indicated by arrows 116, 118, 120 and 122, at any one time, any selected one of insertable rigid rod 102, insertable microwave-radiator assembly 104 or insertable ultrasonic-imaging transducer assembly 106 may be inserted in minimally-invasive water-cooled insertion-sleeve assembly 124 with attached balloon 236. In one exemplary embodiment, the outer diameter of the insertion-sleeve assembly 124 is equal to or less than 0.1 inch. Water-flow means 126, which is connected to insertion-sleeve assembly 124 with attached balloon 236, controls the water-cooling of insertion-sleeve assembly 124 with attached balloon 236.

Figure 2B:
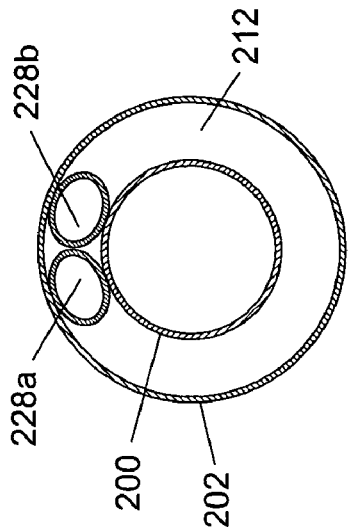
FIG. 2B shows a cross-sectional view of the minimally-invasive, water-cooled insertion-sleeve assembly of FIG. 2A.
Figure 2A:
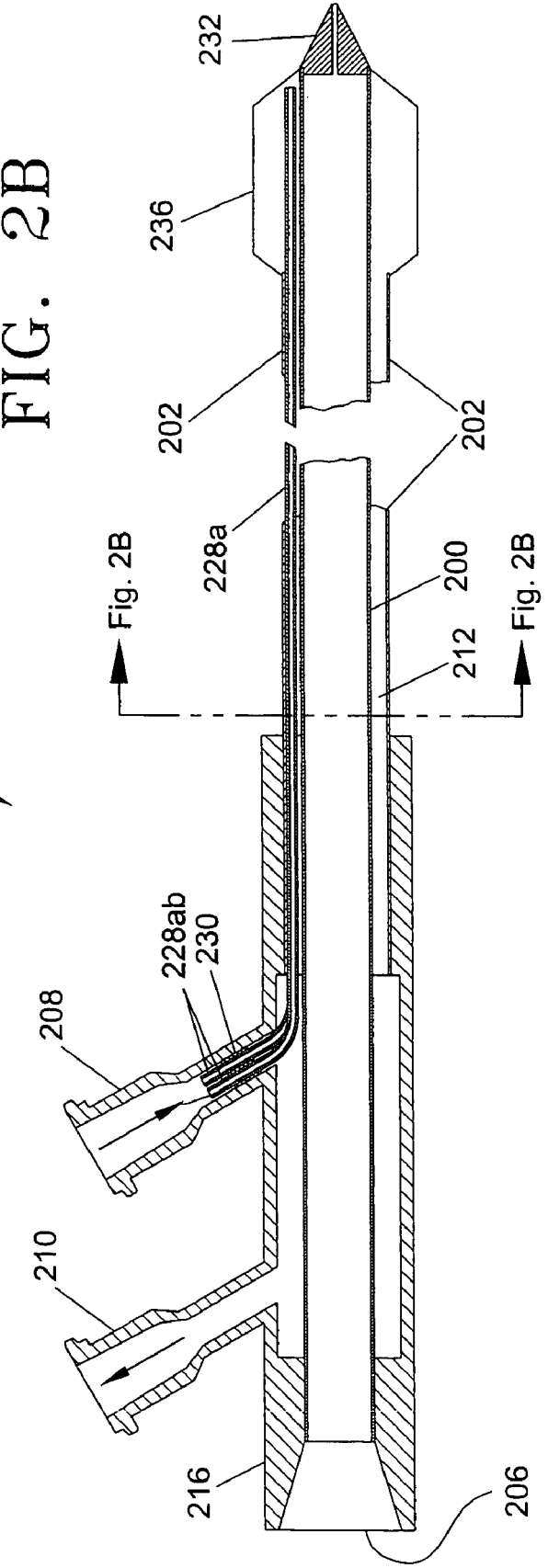
FIG. 2A shows the physical-structure embodiment of the minimally-invasive, water-cooled insertion-sleeve assembly with attached balloon of FIG. 1.

Referring now to FIG. 2A, for the purpose of clarity, there is shown an enlarged sectional view of the physical structure of insertion-sleeve assembly 124 with attached balloon 236. For the purposes of this invention, proximal refers to the portion of the device nearest to the user during use. Distal refers to the portion of the device closest to the patient during use. As indicated in FIG. 2A, insertion-sleeve assembly 124 comprises inner tube 200 situated inside of outer tube 202, which forms a sheath surrounding inner tube 200. In the illustrative embodiment of the invention, outer tube 202 has an inner diameter of 0.088 inch, inner tube 200 has an inner diameter of 0.072 inch, and the thickness of each of these tubes is very small. Therefore, there is a coaxial lumen 212 having an overall width of slightly less than 0.016 inch (i.e., 0.088-0.072 inch) between the inner diameter of outer tube 202 and the outer diameter of inner tube 200. The proximal end of each of tubes 200 and 202 is attached to insertion-sleeve assembly fitting 216.

Insertion sleeve assembly fitting 216 is comprised of a water-coolant input connector 208 (indicated by a downward-pointing arrow), water-coolant output connector 210 (indicated by an upward-pointing arrow) and proximal end opening 206. Proximal end opening 206 allows for insertion of any of the group of separate insertable components 100 into the inner tube 200. Water-coolant input connector 208 and water-coolant output connector 210 provide separate pathways into coaxial lumen 212. As shown in FIG. 2A, water-coolant input connector 208 includes two separate fluid channels 228a and 228b (situated directly behind first fluid channel 228a and, therefore, only partially visible in FIG. 2A). In the illustrative embodiment, each of first and second fluid channels 228a and 228b are comprised of tubes having an inner diameter of only 0.012 inch. Both first and second fluid channels 228a and 228b are joined to the coaxial lumen 212 space and extend toward the distal end of insertion-sleeve assembly 124. Alternative embodiments may include a single or multiple fluid channels.

Further, as shown in FIG. 2A, water coolant seal 230, which is situated within the interior of water-coolant input connector 208 and surrounds both of first and second fluid channels 228a and 228b, limits the input water-coolant to just the interior of first and second fluid channels 228a and 228b. Thus, as shown in the cross-sectional FIG. 2B, the input water-coolant flows toward the distal end of insertion-sleeve assembly 124 through the interior of fluid channels 228a and 228b which are situated within the coaxial lumen 212. The output water-coolant flows back through the portion of the coaxial lumen 212 which is outside of first and second fluid channels 228a and 228b toward the proximal end of insertion-sleeve assembly 124 and then exits through water-coolant output connector 210.

Referring now to FIG. 2C, for the purpose of clarity, there is shown a greatly enlarged view of the most distal section of the physical structure of minimally-invasive, water-cooled insertion-sleeve assembly 124 with attached balloon 236. As indicated in FIG. 2C, the distal end of inner tube 200 is attached to solid, pointed-tip element 232. As shown, element 232 has an optional centrally-located bore hole 234 therethrough. The proximal end of balloon 236 is attached to the outer surface of outer tube 202, and the distal end of balloon 236 is attached to the outer surface of inner tube 200. As indicated in FIG. 2C, the distal end of outer tube 202 is located inside balloon 236 at a position situated only a short distance from the point of attachment of the more proximal end of balloon 236. The distal end of first fluid channel 228a and the distal end of second fluid channel 228b (situated directly behind first fluid channel 228a and, therefore, not visible in FIG. 2C) are also located inside balloon 236, but at respective positions situated near to the distal end of the balloon 236.

Reference is now made to FIG. 2D which shows the most distal section of the physical structure of an alternative embodiment of a minimally-invasive, water-cooled insertion-sleeve assembly 124 without a balloon. In the case of FIG. 2D, distal ends of both inner tube 200 and the outer tube 202 are attached to solid, pointed-tip element 232. Further, in FIG. 2D, the distal end of first fluid channel 228a and the distal end of second fluid channel 228b (situated directly behind fluid channel 228a and, therefore, not visible in FIG. 2D) are spaced a relatively short distance from the attached distal ends of the inner tube 200 and the outer tube 202, thereby allowing input coolant water to flow out from the distal ends of first and second fluid channels 228a and 228b into the coaxial lumen 212. In all other respects, the distal portion of the physical structure of the alternative embodiment of the minimally-invasive, water-cooled insertion-sleeve assembly 124 shown in FIG. 2D is identical to the physical structure of minimally-invasive, water-cooled insertion-sleeve assembly with attached balloon 124 shown in FIG. 2C. Further, the physical structure of the proximal section of the alternative embodiment of the minimally-invasive, water-cooled insertion-sleeve assembly 124 without a balloon (which is identical to the physical structure of the proximal section of minimally-invasive, water-cooled insertion-sleeve assembly 124 with attached balloon 236) is shown in FIG. 2A.

Figure 3A:
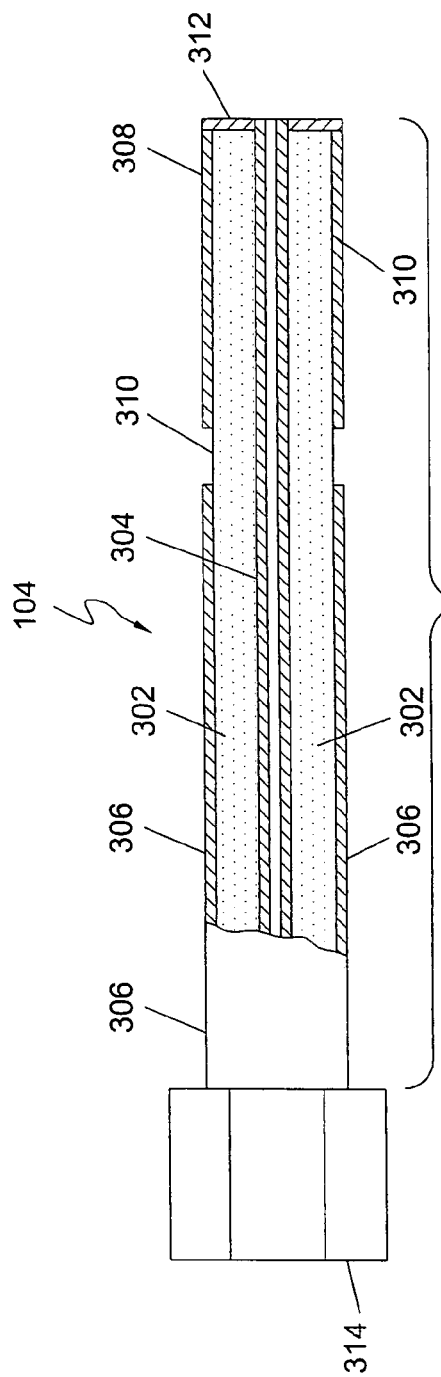
FIG. 3A shows the physical structure of a first embodiment of the insertable microwave-radiator assembly of FIG. 1 prior to insertion in the insertion-sleeve assembly.
Figure 3B:
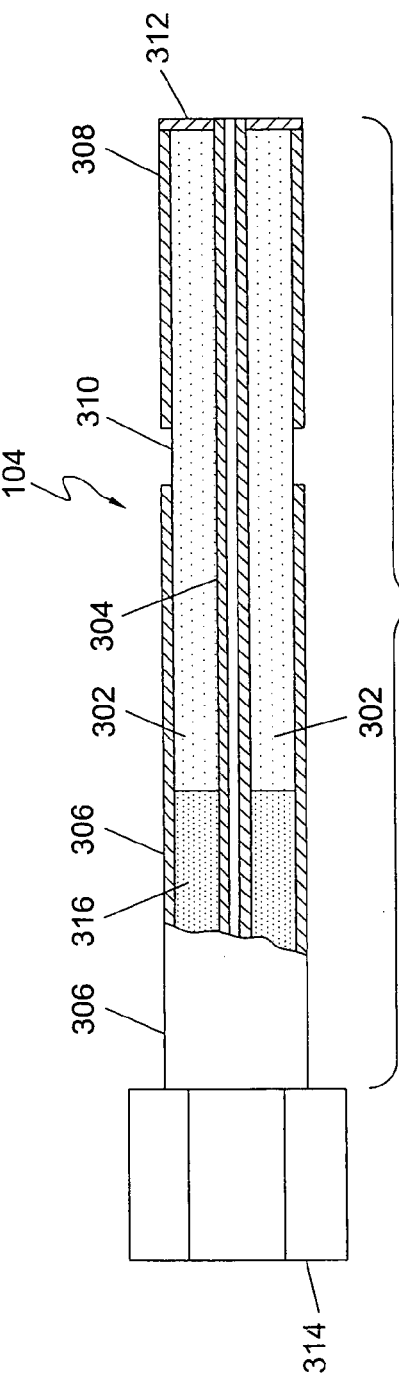
FIG. 3B shows the physical structure of a second embodiment of the insertable microwave-radiator assembly of FIG. 1 prior to insertion in the insertion-sleeve assembly.

Referring to FIGS. 3A and 3B, there are shown, respectively, first and second embodiments of insertable microwave-radiator assembly 104. Each of the first and second embodiments comprises a physical coaxial structure 300 that incorporates a gap antenna 310 for radiating microwave energy supplied as an input to that coaxial structure. The only significant difference between the first embodiment shown in FIG. 3A and the second embodiment shown in FIG. 3B is that the first-embodiment coaxial structure of FIG. 3A uses an externally-situated impedance-matching means, while the second-embodiment coaxial structure of FIG. 3B incorporates internally-situated impedance-matching means.

More specifically, coaxial structure 300 of FIG. 3A comprises a first given length of a commercially available ceramic tubing 302 (shown in section) that has given inner and outer diameters. Commercially available ceramic tubing 302 constitutes the dielectric of coaxial structure 300 and exhibits a relatively high given dielectric constant. Shown entirely in section is metal (preferably copper) cladding the inner surface of ceramic tubing 302 which constitutes the inner conductor 304 of coaxial structure 300. Shown partially in section is first metal (preferably copper) cladding the more proximal portion of the outer surface of ceramic tubing 302 which constitutes the first portion 306 of the outer conductor of coaxial structure 300. Show entirely in section is second metal (preferably copper) cladding the more distal portion of the outer surface of ceramic tubing which constitutes the second portion 308 of the outer conductor of coaxial structure 300.

The first and second portions 306 and 308 of the outer conductor of coaxial structure 300 are longitudinally spaced a certain distance apart from one another thereby to create gap antenna 310 for radiating microwave energy therefrom in response to microwave energization of coaxial structure 300. Shown entirely in section is a metallic (preferably copper) disk 312 cladding the distal end of ceramic tubing 302, which (1) mechanically supports second portion 308 of the outer conductor and (2) electrically shorts the distal ends of the inner and outer conductors of coaxial structure 300. Coaxial structure 300 further comprises coaxial connector 314 for connecting the proximate end of coaxial structure 300 to the distal end of standard 50 ohm impedance coaxial cable connection.

The advantage of the first embodiment of coaxial structure 300 shown in FIG. 3A is that because dielectric comprises commercially-available ceramic tubing 302, it does not have to be machined to proper shape. However, the impedance of coaxial structure 300, which is determined by (1) the dielectric constant of ceramic tubing 302 and (2) the respective outer diameter of inner conductor 304 and the inner diameters of first and second portions 306 and 308 of the outer conductor of coaxial structure 300 (which are substantially equal to the inner and outer diameters of ceramic tubing), is only 18 ohms. Thus, the first embodiment of coaxial structure 300 requires relatively complex external impedance-matching means to match the 18 ohm impedance of coaxial structure 300 with the 50 ohm impedance of standard 50 ohm impedance coaxial cable connection 110, which is a disadvantage.

This disadvantage is avoided in the second embodiment of coaxial structure 300 having a physical structure shown in FIG. 3B which employs a relatively simple internal impedance matching means, rather than the relatively complex external impedance-matching means required with the coaxial structure 300 shown in FIG. 3A. More specifically, coaxial structure 300 comprises a second given length of commercially-available ceramic tubing 302 (which is shorter than the first given length of commercially-available ceramic tubing 302 illustrated in FIG. 3A) in series with impedance-matching ceramic tubing 316 having a length and dielectric constant which is electrically equal to one-quarter wavelength at the operating microwave frequency from microwave generator and control means 108. In all other respects the physical structures of the first and second embodiments of coaxial structures 300 are the same as one another. Impedance-matching ceramic tubing 316 comprises a ceramic having a given dielectric constant which is sufficiently lower than the dielectric constant of commercially-available ceramic tubing 302 to provide an impedance of substantially 30 ohms (i.e., 30 is equal to the square-root of the product of 18×50=900). Although ceramic having the desired given dielectric constant is available, it is not commercially available as tubing having the desired inner and outer diameters. Therefore, to provide impedance-matching ceramic tubing 316, it is necessary to custom machine the tubing to the proper shape and size, which is a disadvantage.

Figure 4:
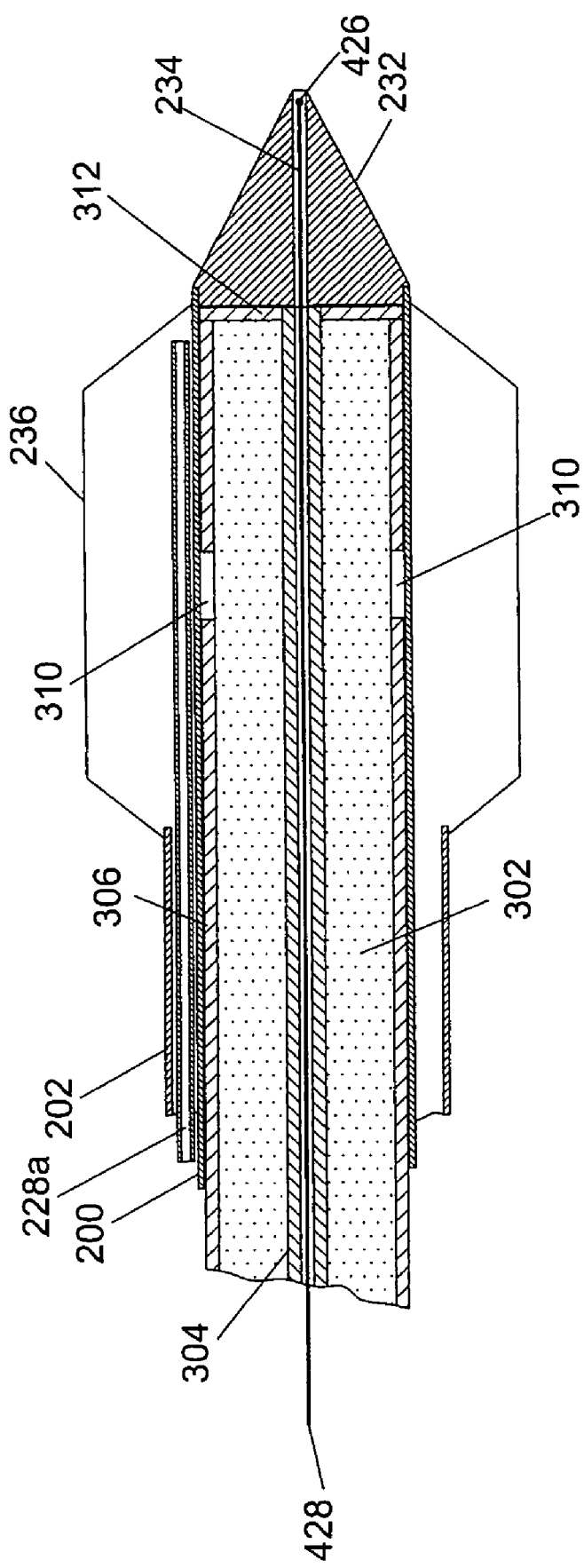
FIG. 4 shows the first embodiment of the insertable microwave-radiator assembly of FIG. 3A, subsequent to insertion in the insertion-sleeve assembly.

FIG. 4 shows the insertable coaxial structure 300 (described above in connection with FIG. 3A) inserted within the distal section of insertion sleeve assembly 124 with attached balloon 236 (described above in connection with FIG. 2A). In FIG. 4, the distal section of insertion sleeve assembly 124 with attached balloon 236 is shown as comprising inner tube 200, outer tube 202, visible fluid channel 228a and fluid channel 228b (not shown). Further, in FIG. 4, the distal section of insertion sleeve assembly 124 comprises attached balloon 236 and solid, pointed-tip element 232 attached to the distal end of inner and outer tubes 200 and 202. As shown, element 232 has centrally-located bore hole 234 therethrough. Situated within bore hole 234, close to the distal end of pointed-tip element 232, is optional thermistor 426. Optional wire 428, extending through the copper tube comprising inner conductor 304, interconnects thermistor 426 to the exterior of the insertable coaxial structures 300, where the output signal from thermistor 426 may be employed to monitor the temperature of tissue being heated by microwave radiation from gap antenna 310 or even to control the microwave power delivered to insertable coaxial structures 300 from microwave generation and control means 108.

If optional thermistor 426 is not employed, pointed-tip element 232 need not incorporate bore hole 234 and inner conductor 304 may comprise a solid copper rod instead of a copper tube.

Figure 5:
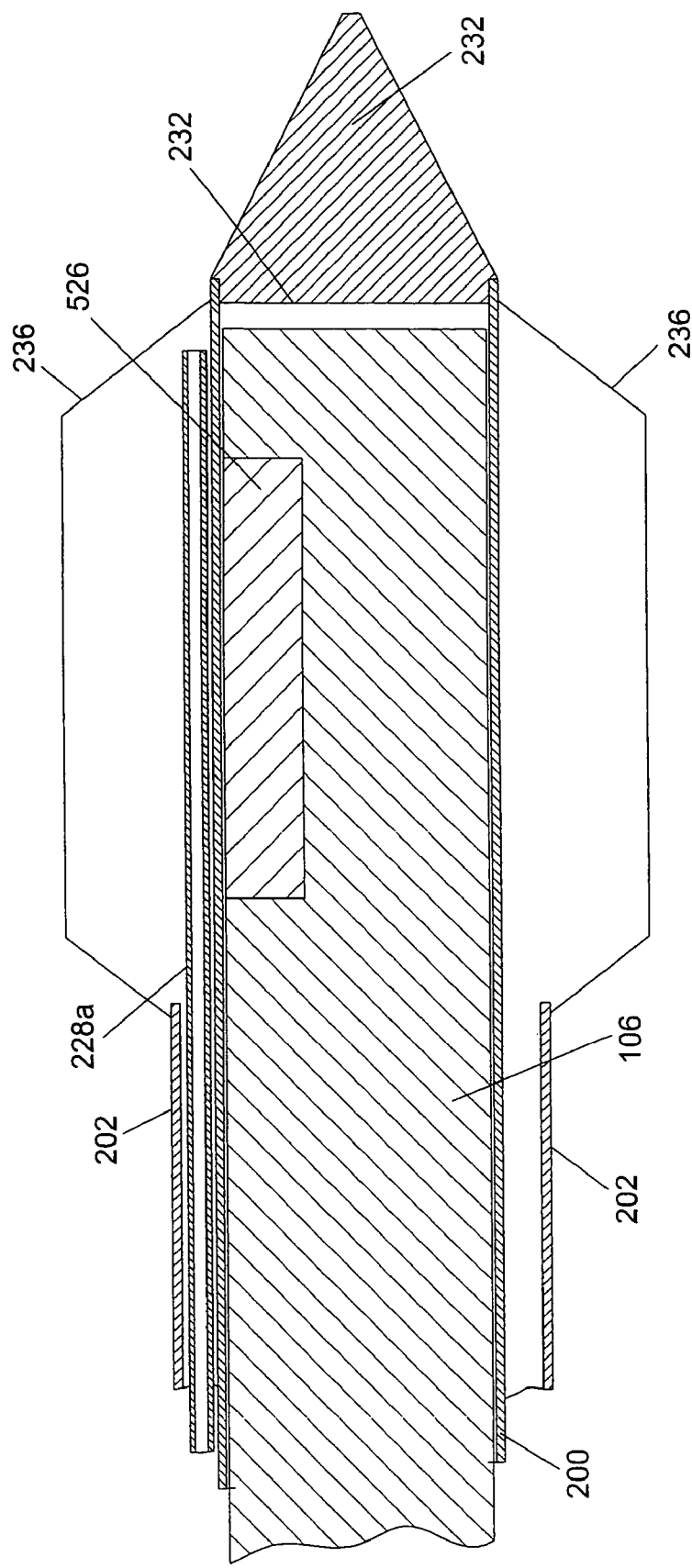
FIG. 5 shows the physical structure of an embodiment of the distal portion of the insertable ultrasonic-imaging transducer assembly of FIG. 1, subsequent to insertion in the insertion-sleeve assembly.

Referring now to FIG. 5, there is shown the physical structure of an embodiment if insertable ultrasonic-imaging transducer assembly 106 is inserted within the distal section of insertion sleeve assembly 124 with attached balloon 236. As shown in FIG. 5, solid, pointed-tip element 232 does not show an optional central bore hole therethrough. However, in practice, solid, pointed-tip element 232 may either (1) incorporate or (2) not incorporate such an optional central bore hole therethrough, since it is not needed for use with inserted ultrasonic-imaging transducer assembly 106.

As shown in FIG. 5, inserted ultrasonic-imaging transducer assembly 106 comprises the combination of ultrasonic lens 526 coupled to ultrasonic transducer means for use in (1) transmitting to targeted tissue of a patient with illuminating ultrasonic wave energy in response to being energized by ultrasonic generation and processing means 112 and (2) focusing received ultrasonic echoes from the targeted tissue and forwarding the focused received ultrasonic echoes to ultrasonic generation and processing means 112 for image processing and display.

Figure 6B:
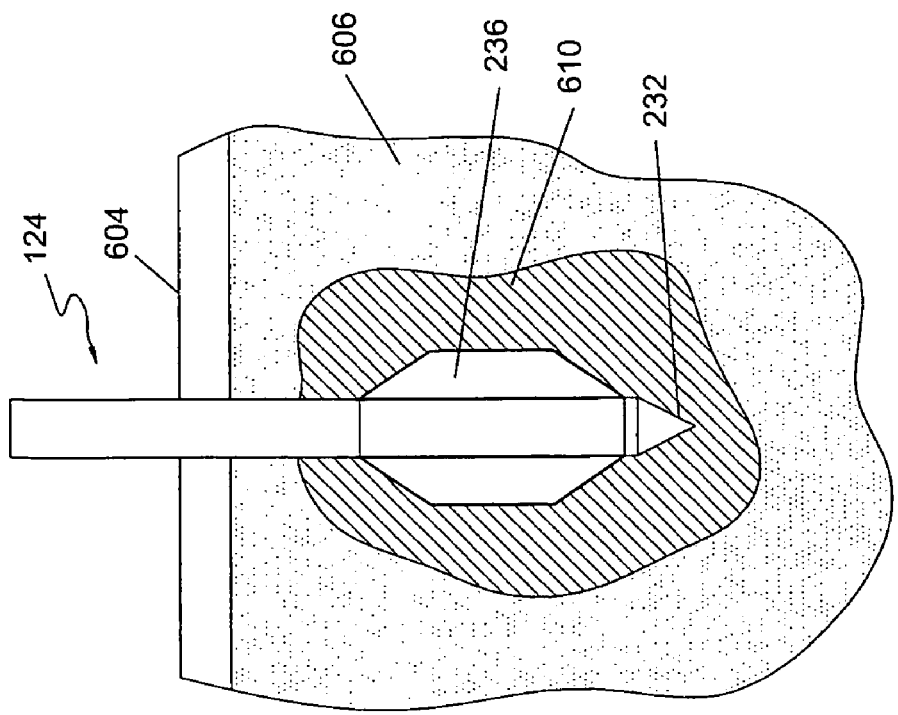
FIG. 6B schematically shows an inflatable balloon probe that has been inserted through the skin of a patient and sub-cutaneous tissue with its balloon fully inflated and pressing against the tumor.
Figure 6A:
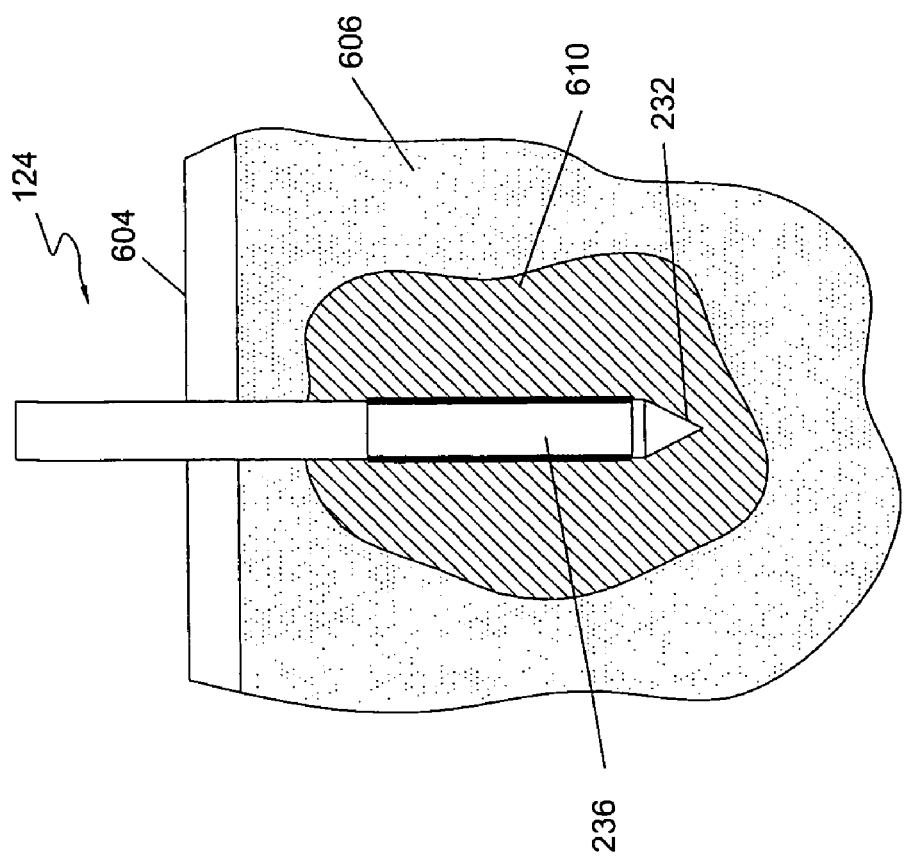
FIG. 6A schematically shows an inflatable balloon probe that has been inserted through the skin of a patient and sub-cutaneous tissue with its balloon in its deflated state situated in a tumor within deep-seated tissue.

Referring now to FIGS. 6A and 6B, schematically illustrate the basic operation of a probe with an attached balloon 236 used in an interstitial microwave system for thermally treating diseased tissue of a patient, such as a deep-seated tumor. In FIG. 6A, pointed-tip element 232 is used to puncture skin 604 and the underlying sub-cutaneous tissue 606 and then position the probe so that its deflated balloon 236 is situated within or in proximity to tumor 610 of the patient being treated. As shown in FIG. 6B, balloon 236 is then inflated to press against tumor 610, prior to tumor 610 being irradiated by microwave energy emitted from an antenna within the probe. The following irradiation of tumor 610 preferably heats the tissue of tumor 610 in proximity to inflated balloon 236 to a temperature sufficient to cause ablation and necrosis of proximate tumor cells. Balloon 236 may then be deflated and the probe removed from the body of the patient.

It is apparent that minimally-invasive water-cooled sleeve assembly 124 with attached balloon 236, comprising the probe of the present invention, may be insufficiently stiff by itself, with its balloon 236 in a deflated state, to first puncture skin 604 and then push through underlying sub-cutaneous tissue 606 and position itself so that its deflated balloon 236 is situated within or in proximity to tumor 610 of the patient being treated. Therefore, prior to any attempt to puncture skin 604, insertable rigid rod 102, which is preferably a stainless-steel rod, is inserted within sleeve assembly 124 to provide the necessary stiffness. Then with rigid rod 102 inserted, sleeve assembly 124, with its balloon 236 in a deflated state, is used to first puncture skin 604 and then push through underlying sub-cutaneous tissue 606 and position itself so that its deflated balloon 236 is situated in proximity to tumor 610 of the patient being treated.

Once deflated balloon 236 has been situated within or in proximity to tumor 610 of the patient being treated inserted rigid rod 102 is removed from sleeve assembly 124 and insertable microwave-radiator assembly 104 is inserted within sleeve assembly 124 as a replacement for rigid rod 102. Then, water-flow means is operated to effect a continuous flow of water coolant through first and second fluid channels 228a and 228b, balloon 236 of sleeve assembly 124, with the water coolant flowing through the space of coaxial lumen 212 to exit through output connector 210. This continuous flow of water coolant is effective in first inflating balloon 236 and then maintaining balloon 236 inflated. While balloon 236 is inflated, microwave energy from microwave generation and control means 108 is supplied to inserted microwave-radiator assembly 104. This results in gap antenna 310 radiating microwave energy to the targeted tissue of tumor 610 to effect the heating of the targeted tissue of tumor 610 to a temperature sufficient to cause ablation and necrosis thereof.

The continuous flow of water coolant makes it possible to supply gap antenna 310 relatively-high microwave power (50 to 100 watts) from microwave generation and control means 108 for heating the targeted tissue of tumor 610 to a temperature sufficient to cause ablation and necrosis thereof without, at the same time, causing non-targeted tissue in the immediate vicinity of the inserted probe being overheated to an unsafe temperature. Further, temperature data supplied from thermistor 426 may be used to lower the microwave power generated by microwave generation and control means 108 or, alternatively, turn off the generation of all microwave power by microwave generation and control means 108 to prevent non-targeted tissue in the immediate vicinity of the inserted probe from being overheated to an unsafe temperature. An additional benefit of employing a relatively-high microwave power of 50 to 100 watts is that this microwave power may be supplied for only a relatively short period of time (about 5 minutes) and still result in ablation and necrosis of the targeted tissue of tumor 610. This relatively short period of time limits the amount of unwanted heating by conduction of non-targeted tissue surrounding tumor 610. The use of relatively high microwave power and relatively short period of time radiation of tumor tissue is particularly suitable for use with a large-sized (up to a 4 centimeter-sized dimension) tumor (such as a liver tumor).

Ultrasonic-imaging transducer assembly 106 may be employed (1) prior to the commencement of tumor 610 being irradiated, (2) subsequent to the commencement, but prior to the completion, of tumor 610 being irradiated or (3) subsequent to the completion of tumor 610 being irradiated. In the first case, after sleeve assembly 124 has been installed and rigid rod 102 has been removed from sleeve assembly 124, insertable ultrasonic-imaging assembly 106 may be inserted within sleeve assembly 124 as a replacement for rigid rod 102. Water or other acoustical enhancing medium may be introduced into the insertion sleeve assembly 124 as previously described to increase echogenicity of the targeted tissue and provide the operator of ultrasonic generation and processing means 112 with an image display of tumor 610 prior to any irradiation thereof. The image display may be used by the operator in deciding the microwave-power and period-of-time settings to be employed by microwave generation and control means 108. Only then is ultrasonic-imaging assembly 106 replaced by the insertion of microwave-radiator assembly 104 inserted within sleeve assembly 124. The second case is applicable where a problem occurs during the irradiation of tumor 106. In the second case, microwave-radiator assembly 104 is replaced by the insertion of ultrasonic-imaging assembly 106 inserted within sleeve assembly 124 followed by the image display of the current condition of tumor 610. In the third case, microwave-radiator assembly 104 is replaced by the insertion of ultrasonic-imaging assembly 106 inserted within sleeve assembly 124 followed by the image display after ablation of the tissue of tumor 610 has occurred.

While the illustrative embodiment of the present invention employs a thermistor to determine tissue temperature, there are other known devices for determining tissue temperature that may be substituted for a thermistor. In this regard, incorporated by reference herein is the radiometer means disclosed in the aforementioned U.S. Pat. No. 6,847,848.

In all the above described embodiments of the present invention, water can be employed as the fluid coolant because water has a high heat capacity. However, in general, the fluid coolant may be any desired liquid coolant or any desired pumped-gas coolant. Further, while insertable microwave-radiator assembly 104 is essential in the group of separate individual insertable components 100, this group could comprise one or more other components from those shown in FIG. 1. For instance, a miniature camera and light source that can be used to view and image diseased tissue through clear tubing, and clear fluid coolant can be employed as an additional one of the group of separate individual insertable components 100. Also, the physical structure of insertion-sleeve assembly 124 and the insertable elements of the group of separate individual insertable components 100 can be modified to have a slight curvature. (similar to the curvature of a scimitar) which would permit insertion-sleeve assembly 124 to go around obstacles such as bone during the process of its insertion through the sub-cutaneous tissue of the patient. In this regard, rigid rod 102 can have the appropriate curvature, and the ceramic dielectric of the coaxial structure comprising microwave-radiator assembly 104 can be made from powdered ceramic, rather than solid ceramic.

What is claimed is:

1. A microwave probe system for thermally treating subcutaneous tissue of a patient comprising:
    a fluid-coolable insertion sleeve assembly into which at least a portion of a microwave radiator assembly may be inserted, wherein the microwave-radiator assembly comprises a coaxial structure having a proximal end and a distal end, and wherein the coaxial structure comprises:
        a gap antenna;
        an outer conductor having a first portion and a second portion, wherein the second portion has a proximal end and a distal end;
        a ceramic tube having a proximal end and a distal end, wherein the ceramic tube constitutes a dielectric of the coaxial structure, and wherein the ceramic tube comprises:
            an inner metallic cladding, wherein the inner metallic cladding comprises an inner conductor having a proximal end and a distal end, and
            an outer metallic cladding having a proximal portion and a distal portion, wherein the proximal portion of the outer metallic cladding constitutes the first portion of the outer conductor, wherein the distal portion of the outer metallic cladding constitutes the second portion of the outer conductor, and wherein the proximal and distal portions of the outer metallic cladding are longitudinally spaced apart to define the gap antenna;
        a metallic disk, wherein the metallic disk comprises cladding at the distal end of the ceramic tube, and wherein the cladding connects the distal end of the inner conductor to the distal end of the second portion of the outer conductor, thereby electrically shorting the distal ends of the inner and outer conductors; and
        a coaxial connector, wherein the coaxial connector is attached to the proximal end of the coaxial structure.

2. The microwave probe system of claim 1, wherein the probe has an outer diameter that is no greater than 0.12 inch in size.

3. The microwave probe system of claim 1, wherein the fluid-coolable insertion sleeve assembly comprises;
    an outer tube having a proximal end and a distal end;
    an inner tube coaxially arranged within the outer tube to provide a coaxial lumen between the inner and outer tubes;
    an opening at the proximal end of the fluid-coolable insertion sleeve assembly whereby any one of the group of separate insertable components may be inserted within the inner tube; and
    at least one fluid channel within the coaxial lumen for providing a coolant to the insertion sleeve assembly.

4. The microwave probe system of claim 3, wherein the coolant exits the insertion sleeve assembly through the coaxial lumen.

5. The microwave probe system of claim 4, further comprising:
a balloon having a proximal end and a distal end and an interior, wherein the proximal end of the balloon is attached to the outer tube and the distal end of the balloon is attached to the inner tube,
wherein the outer tube and the at least one fluid channel extend into the interior of the balloon, and
wherein the coolant flowing in the at least one fluid channel flows into the interior of the balloon, thereby inflating the balloon, and then exits from the balloon through the coaxial lumen.

6. The microwave probe system of claim 5, wherein the coolant is water.

7. The microwave probe system of claim 6, further comprising: a water-flow means for maintaining a continuous flow of the coolant through (1) each of the at least one fluid channel, (2) the interior of the balloon and (3) the coaxial lumen.

8. The microwave probe system of claim 4, wherein the coolant is water.

9. The microwave probe system of claim 3, wherein the coolant is water.

10. The microwave probe system of claim 1, wherein a penetrating tip is attached to the distal end of the fluid-coolable insertion-sleeve assembly.

11. The microwave probe system of claim 10, wherein the distal end of the outer tube is attached to the penetrating tip, thereby creating a distal end to the coaxial lumen, wherein the distal end of the fluid channel is spaced a distance proximally from the distal end of the coaxial lumen such that the distance is sufficient to provide cooling to the entire length of the fluid-coolable insertion-sleeve assembly.

12. The microwave probe system of claim 10, wherein:
the coaxial structure is positioned within the fluid-coolable insertion sleeve assembly;
the penetrating tip includes a bore hole therethrough; and
wherein the microwave probe system further comprises a thermistor situated within the bore hole, wherein the thermistor is attached to a wire, and wherein the wire extends through the coaxial structure and is capable of forwarding temperature data from the thermistor to outside of the coaxial structure.

13. The microwave probe system of claim 12, further comprising:
a microwave generation and control means having an output therefrom coupled to the coaxial connector for supplying a controlled amount of microwave energy to the coaxial structure thereby to effect radiation of microwave energy from the gap antenna; and
wherein the wire is capable of forwarding the temperature data from the thermistor to the microwave generation and control means to effect control of the amount of microwave energy supplied to the inserted coaxial structure.

14. The microwave probe system defined in claim 1, wherein:
the fluid-coolable insertion sleeve assembly is a water-coolable insertion sleeve assembly.

15. The microwave probe system of claim 1, wherein the inner and outer metallic cladding and the metallic disk are comprised of copper.

16. The microwave probe system of claim 1, wherein:
the coaxial connector is capable of being connected to an external standard coaxial cable that exhibits an impedance of substantially 50 ohms; and
the ceramic tube exhibits a first relatively high value of dielectric constant resulting in the coaxial structure exhibiting a given impedance which is substantially lower than 50 ohms, whereby utilizing the coaxial structure requires external impedance-matching means to be employed.

17. The microwave probe system of claim 16, wherein: the given impedance is substantially 18 ohms.

18. The microwave probe system of claim 1, wherein;
the coaxial connector is capable of being connected to an external standard coaxial cable that exhibits an impedance of substantially 50 ohms;
the distal portion of the ceramic tube exhibits a first relatively high value of dielectric constant; and
the proximal portion of the ceramic tube exhibits a second relatively low value of dielectric constant resulting in the coaxial structure exhibiting a given impedance of substantially 50 ohms, whereby utilizing the coaxial structure does not require external impedance-matching means to be employed, 19. The microwave probe system of claim 18, wherein:
the distal portion of the ceramic tube exhibits an impedance which is substantially 18 ohms; and
the proximal portion of the ceramic tube exhibits an impedance which is substantially 30 ohms.

20. The microwave probe system of claim 1, further comprising:
a microwave generation and control means having an output therefore coupled to an input of the microwave-radiator assembly while the microwave-radiator assembly is positioned within the fluid-coolable insertion sleeve assembly, thereby effecting energization of the microwave-radiator assembly with microwave energy and subsequent radiation of the microwave energy from the microwave-radiator assembly.

21. A method for thermally treating subcutaneous tissue of a patient, comprising:
providing a probe system, wherein the system comprises a fluid-coolable insertion-sleeve assembly into which at least a portion of a microwave radiator assembly may be inserted, wherein the microwave-radiator assembly comprises a coaxial structure having a proximal end and a distal end, and wherein the coaxial structure comprises:
a gap antenna:
an outer conductor having a first portion and a second portion, wherein the second portion has a proximal end and a distal end;
a ceramic tube having a proximal end and a distal end, wherein the ceramic tube constitutes a dielectric of the coaxial structure, and wherein the ceramic tube comprises:
an inner metallic cladding, wherein the inner metallic cladding comprises an inner conductor having a proximal end and a distal end,
an outer metallic cladding having a proximal portion and a distal portion, wherein the proximal portion of the outer metallic cladding constitutes the first portion of the outer conductor, wherein the distal portion of the outer metallic cladding constitutes the second portion of the outer conductor, and wherein the proximal and distal portions of the outer metallic cladding are longitudinally-spaced to define the gap antenna;
a metallic disk, wherein the metallic disk comprises cladding at the distal end of the ceramic tube, and wherein the cladding connects the distal end of the inner conductor to the distal end of the second portion of the outer conductor, thereby electrically shorting the distal ends of the inner and outer conductors; and a coaxial connector, wherein the coaxial connector is attached to the proximal end of the coaxial structure;

placing the fluid-coolable insertion-sleeve assembly in a desired position within the tissue;

inserting the microwave-radiator assembly within the fluid-coolable sleeve assembly;

providing a coolant;

flowing the coolant through the fluid-coolable sleeve assembly; and supplying the microwave-radiator assembly with microwave energy to heat the tissue by absorbed microwave radiation from the microwave-radiator assembly.

22. The method of claim 21, wherein the fluid-coolable insertion-sleeve assembly includes a balloon attached thereto, and wherein the step of flowing coolant through the fluid-coolable sleeve assembly further comprises:

inflating the balloon in response to the flow of coolant into the interior of the balloon; and deflating the balloon in response to the termination of the flow of coolant.

23. The method of claim 22, wherein inflation of the balloon compresses the tissue outwardly.

24. The method of claim 21, wherein the step of supplying the microwave-radiator assembly with microwave energy comprises supplying microwave energy of a predetermined value for a predetermined interval of time to heat the tissue to a sufficiently high temperature to effect ablation of the tissue.

25. The method of claim 24, wherein the predetermined value of microwave power is sufficiently high to effect ablation and the predetermined interval of time is sufficiently short to prevent heating to an unsafe temperature.

26. The method of claim 24, wherein the predetermined value of microwave power is between 50 and 100 watts, and the predetermined interval of time is no greater than 7 minutes.

* * * * *